US009463106B2

(12) United States Patent
Khieu et al.

(10) Patent No.: US 9,463,106 B2
(45) Date of Patent: Oct. 11, 2016

(54) CATHETER WITH RELEASABLE BALLOON AND RELATED METHODS

(71) Applicant: Boston Scientific Scimed, Inc., Maple Grove, MN (US)

(72) Inventors: Aaron Khieu, Maple Grove, MN (US); Daniel Horn, Shoreview, MN (US); The Thomas Trinh Tran, Coon Rapids, MN (US); Shannon Stroud, Osseo, MN (US); John Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 322 days.

(21) Appl. No.: 14/023,106

(22) Filed: Sep. 10, 2013

(65) Prior Publication Data

US 2014/0074142 A1    Mar. 13, 2014

Related U.S. Application Data

(60) Provisional application No. 61/699,029, filed on Sep. 10, 2012.

(51) Int. Cl.
*A61M 29/00* (2006.01)
*A61F 5/00* (2006.01)
*A61M 25/10* (2013.01)

(52) U.S. Cl.
CPC ............. *A61F 5/003* (2013.01); *A61F 5/0036* (2013.01); *A61F 5/0089* (2013.01); *A61M 25/10* (2013.01); *A61M 2025/1054* (2013.01); *A61M 2210/1053* (2013.01)

(58) Field of Classification Search
CPC .................... A61M 25/10; A61M 2025/1054; A61F 5/0003; A61F 5/0013; A61F 5/003–5/0046; A61F 5/0076–5/0079; A61F 5/0089; A61F 2005/0016–2005/0023

USPC .......... 606/1, 108, 191–192, 195; 604/96.01, 604/104, 907
See application file for complete search history.

(56) References Cited

U.S. PATENT DOCUMENTS 4,364,392 A    12/1982  Strother et al.
4,517,979 A     5/1985  Pecenka
(Continued)

FOREIGN PATENT DOCUMENTS

WO    WO 88/03817 A1     6/1988
WO    WO 2006/129419 A1  12/2006
WO    WO 2009/059803      5/2009

OTHER PUBLICATIONS

International Search Report for corresponding international application PCT/US2013/059035, mailed Nov. 4, 2013, 6 pages.

*Primary Examiner* — Victor Nguyen
*Assistant Examiner* — Jonathan Hollm
(74) *Attorney, Agent, or Firm* — Bookoff McAndrews, PLLC (57) ABSTRACT

Various embodiments of a balloon catheter and related methods are disclosed. In particular, one exemplary embodiment of a balloon catheter may include a balloon having an inlet opening for receiving inflation fluid and a one-way valve disposed in the inlet opening to allow inflow of the inflation fluid into the balloon while substantially preventing backflow of the inflation fluid from the balloon. The catheter may also include an elongated shaft comprising a proximal end, a distal end, and a lumen extending between the proximal and distal ends. The shaft may be configured to supply the inflation fluid to the balloon through the lumen and to releasably couple the balloon to the distal end of the shaft.

20 Claims, 5 Drawing Sheets

(56) References Cited

U.S. PATENT DOCUMENTS

| | | | | | |
|---|---|---|---|---|---|
| 4,545,367 | A | * | 10/1985 | Tucci | 128/898 |
| 4,694,827 | A | * | 9/1987 | Weiner | A61F 5/0036 604/909 |
| 4,925,446 | A | * | 5/1990 | Garay et al. | 604/103.02 |
| 5,002,556 | A | * | 3/1991 | Ishida et al. | 606/191 |
| 5,084,061 | A | | 1/1992 | Gau et al. | |
| 5,601,600 | A | * | 2/1997 | Ton | 606/206 |
| 6,419,699 | B1 | | 7/2002 | Schuessler | |
| 6,547,804 | B2 | * | 4/2003 | Porter | A61B 17/12113 606/195 |
| 7,235,082 | B2 | * | 6/2007 | Bartish et al. | 606/99 |
| 2005/0033332 | A1 | * | 2/2005 | Burnett | A61F 5/0073 606/156 |
| 2005/0288706 | A1 | | 12/2005 | Widomski et al. | |
| 2009/0036877 | A1 | * | 2/2009 | Nardone et al. | 606/1 |
| 2009/0275973 | A1 | | 11/2009 | Chen et al. | |
| 2010/0076481 | A1 | * | 3/2010 | Stephens et al. | 606/192 |
| 2012/0191125 | A1 | * | 7/2012 | Babkes | A61F 5/0036 606/192 |
| 2013/0237952 | A1 | * | 9/2013 | Takagi et al. | 604/500 |

* cited by examiner

FIG. 7

CATHETER WITH RELEASABLE BALLOON AND RELATED METHODS

CROSS-REFERENCE TO RELATED APPLICATIONS

This application claims the benefit of priority from U.S. Provisional Application No. 61/699,029, filed Sep. 10, 2012, the entirety of which is incorporated by reference herein.

FIELD OF THE INVENTION

Various embodiments of the present disclosure relate generally to medical devices and related methods. More specifically, particular embodiments of the present disclosure relate to a balloon catheter and related methods for use in, for example, delivery and placement of a gastric balloon.

DESCRIPTION OF RELATED ART

Obesity is a leading cause of preventable death worldwide. Obesity is a complex medical condition in which excess fat accumulated in a body may cause an adverse effect on health and increase the likelihood of various diseases, including heart disease, hypertension, type II diabetes, sleep apnea, gallstones, and osteoarthritis. Current treatments for obesity range from non-surgical, behavioral modification (e.g., dieting and exercise) and pharmacotherapy to various types of surgical treatments. In general, non-surgical treatments are used for patients with a body mass index (BMI) of less than 40 and achieve relatively short-term and limited weight reduction. Surgical treatments, generally performed on morbidly obese patients with a BMI greater than 40, may include various types of bariatric surgery with varying efficacy and invasiveness levels.

Examples of highly invasive surgical treatments include gastroplasty surgery for reducing the size of the stomach to restrict the food-consumption capacity and gastric bypass surgery for rearranging a part of the digestive track to decrease the nutrient absorption. While being high in efficacy, the surgical treatments may lead to serious complications and adverse effects due to the highly invasive nature of the procedures. In addition, these treatments are normally irreversible.

As a less invasive intervention for the treatment of obesity, a concept of gastric balloon treatment has been proposed. Gastric balloon treatment involves placing a deflated balloon in the stomach and inflating it with fluid to occupy a part of the gastric volume inside the stomach, reducing the amount of food intake. Despite extensive research, however, there still exist unmet technical needs to improve the delivery operations, as well as efficacy, of gastric balloon treatment.

SUMMARY OF THE INVENTION

Therefore, various exemplary embodiments of the present disclosure may provide a device and method for facilitating the delivery and inflation of a gastric balloon to treat obesity. In particular, certain embodiments of the present disclosure may include a balloon catheter having a gastric balloon attached to the distal end of the balloon catheter and a suitable release mechanism to selectively detach the balloon. The catheter may be configured to supply inflation fluid to the balloon while the balloon is attached to the catheter. Thus, a balloon catheter consistent with the present disclosure may provide a complete device that enables delivery, inflation, and placement of a gastric balloon, which may greatly simplify the operation of gastric balloon treatment without adversely affecting its efficacy.

While the exemplary embodiments of the present disclosure are described in connection with a balloon catheter for treatment of obesity, it should be understood that other embodiments consistent with the present disclosure may be used in other suitable medical and non-medical applications and fields. For example, certain embodiments consistent with the present disclosure may be used in connection with any medical procedure that may require a balloon or an inflatable part, including breast augmentation surgery to insert a breast implant or balloon temponade to stop refractory bleeding.

To attain the advantages and in accordance with the purpose of the invention, as embodied and broadly described herein, one exemplary aspect of the invention may provide a catheter comprising a balloon having an inlet opening for receiving inflation fluid and a one-way valve disposed in the inlet opening. The one-way valve may allow inflow of the inflation fluid into the balloon while substantially preventing backflow of the inflation fluid from the balloon. The catheter may also include an elongated shaft comprising a proximal end, a distal end, and a lumen extending between the proximal and distal ends. The shaft may be configured to supply the inflation fluid to the balloon through the lumen and to releasably couple the balloon to the distal end of the shaft.

In another exemplary aspect, the catheter may include a plunger movably disposed inside the lumen to actuate a release of the balloon from the distal end of the shaft. The plunger may define an internal fluid channel having one end configured to connect to a source of the inflation fluid and the other end configured to supply the inflation fluid to the inlet opening of the balloon.

According to one exemplary aspect, the balloon may include a connector body configured to releasably engage the distal end of the shaft, where the connector body may define the inlet opening. The distal end of the shaft may include a movable pin configured to engage a slot formed in the connector body.

In some exemplary aspects, the movable pin may be movable from a first position in which the movable pin engages the slot to couple the balloon to the shaft to a second position in which the movable pin disengages the slot to release the balloon from the shaft. The movable pin may be connected to a spring biased to the second position. In another exemplary aspect, the catheter may include a plunger movably disposed inside the lumen and configured to actuate movement of the movable pin to disengage the movable pin from the slot to release the balloon from the distal end of the shaft.

In still another exemplary aspect, the one-way valve may be attached to the connector body to selectively close the inlet opening. The connector body may include a hollow tube configured to receive the distal end of the shaft.

In yet still another exemplary aspect, the one-way valve may include a flap valve mounted to the inlet opening.

According to one exemplary aspect, the balloon, when inflated, may include two side portions and a narrow center portion interconnecting the two side portions.

Another exemplary aspect of the present disclosure may provide a method of placing a balloon inside a patient's body. The method may include: inserting into a body passage an elongated shaft having an inflatable balloon releasably coupled to a distal end of the shaft; guiding the shaft to place the balloon at a desired target location inside the patient's body; supplying inflation fluid to the balloon through an internal lumen of the shaft while the balloon is attached to the distal end of the shaft, wherein an inlet opening of the balloon comprises a one-way valve configured to allow inflow of the inflation fluid into the balloon while substantially preventing backflow of the inflation fluid from the balloon; and releasing the inflated balloon from the distal end of the shaft.

In still another exemplary aspect, releasing the balloon from the distal end of the shaft may comprise actuating a plunger movably disposed inside the shaft to release the releasable coupling between the balloon and the distal end of the shaft.

According to some exemplary aspects, the balloon may comprise a connector body configured to releasably couple the distal end of the shaft, and the inlet opening is disposed in the connector body. The releasable coupling between the balloon and the distal end of the shaft may comprise a movable pin configured to engage a slot formed in the connector body, wherein the movable pin is movable from a first position in which the movable pin engages the slot to couple the balloon to the shaft to a second position in which the movable pin disengages the slot to release the balloon from the shaft.

In one exemplary aspect, releasing the balloon from the distal end of the shaft may comprise moving a plunger disposed inside the shaft to cause movement of the movable pin from the first position to the second position.

According to another exemplary aspect, the connector body may comprise a hollow tube configured to receive the distal end of the shaft.

In still another exemplary aspect, the one-way valve may comprise a flap valve mounted to the inlet opening.

In still yet another exemplary aspect, the balloon may be a gastric balloon, and the step of inserting the shaft into the body passage may comprise inserting the shaft transorally into the patient's stomach.

Additional objects and advantages of the disclosed invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various exemplary embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

FIGS. 1-4B illustrate a balloon catheter 10 for use in, for example, delivering and inflating a gastric balloon in a patient's stomach, according to one exemplary embodiment of the present disclosure. Balloon catheter 10 may include an elongated shaft 40 defining an internal lumen 45, a plunger 20 movably disposed inside lumen 45, and a balloon 80 releasably coupled to a distal end portion 49 of shaft 40.

Figure 1:
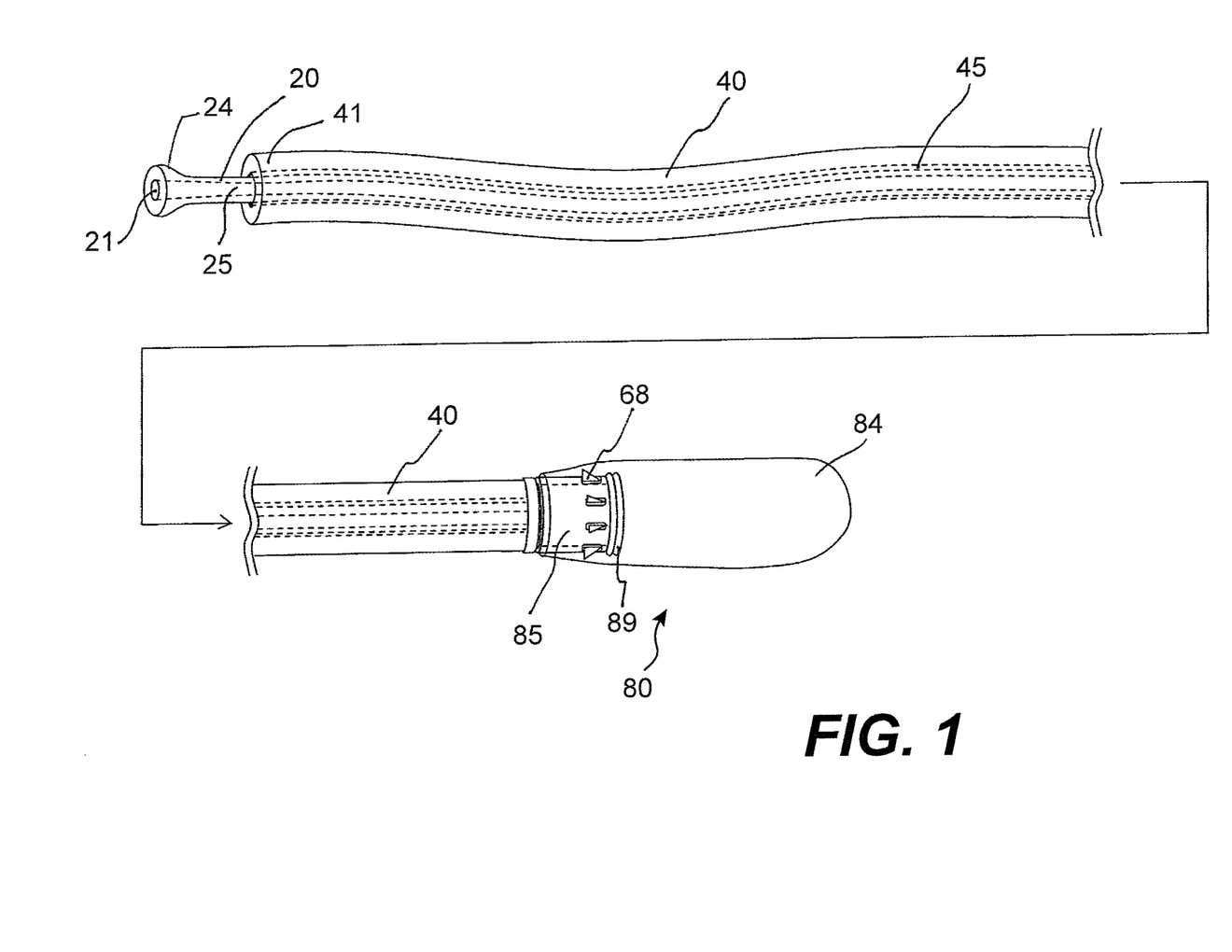
FIG. 1 is a schematic perspective view of a balloon catheter having a detachable balloon in a deflated state, according to an exemplary embodiment of the present disclosure.

Shaft 40 may be an elongated tube having sufficient flexibility to traverse through tortuous anatomy of a patient's body. The degree of flexibility and the overall dimension (e.g., length and thickness) of shaft 40 may vary depending upon the type of procedure being performed with balloon catheter 10. Although not shown, a proximal end portion 41 of shaft 40 may include a suitable grip-enhancing member, including, but not limited to, a finger flange, a finger rest, or a finger ring, or a handle to facilitate the movement of balloon catheter 10, especially in relation to plunger 20.

Plunger 20 may comprise an elongated member disposed inside lumen 45 of shaft 40. Plunger 20 may be configured to move relative to shaft 40 to releasably couple balloon 70 to shaft 40. Plunger 20 may include an internal lumen 25 to supply inflation fluid to balloon 80. The inflation fluid may include, but is not limited to, air, saline solution, or any suitable biocompatible fluid known in the art. In some exemplary embodiments, the inflation fluid may be colored, such as, for example, blue or include substance that may aid visualization of balloon 80, such as, for example, fluorescent or radio-opaque substance. A suitable fluid supply line connected to a source of inflation fluid may be connected to an inlet 21 located at a proximal end portion 24 of plunger 20.

In an alternative embodiment, a separate supply tube may be extended through lumen 45 of shaft 40 to supply inflation fluid to balloon 80. In another exemplary embodiment, shaft 40 may include a T- or Y-connector, where one of the two inlet branches receives plunger 20 and the other inlet branch connects to a fluid supply line.

Proximal end portion 24 may have a shape that makes it easier to manipulate its movement relative to shaft 40. Alternatively or additionally, proximal end portion 24 may have a grip-enhancing member.

Figure 2:
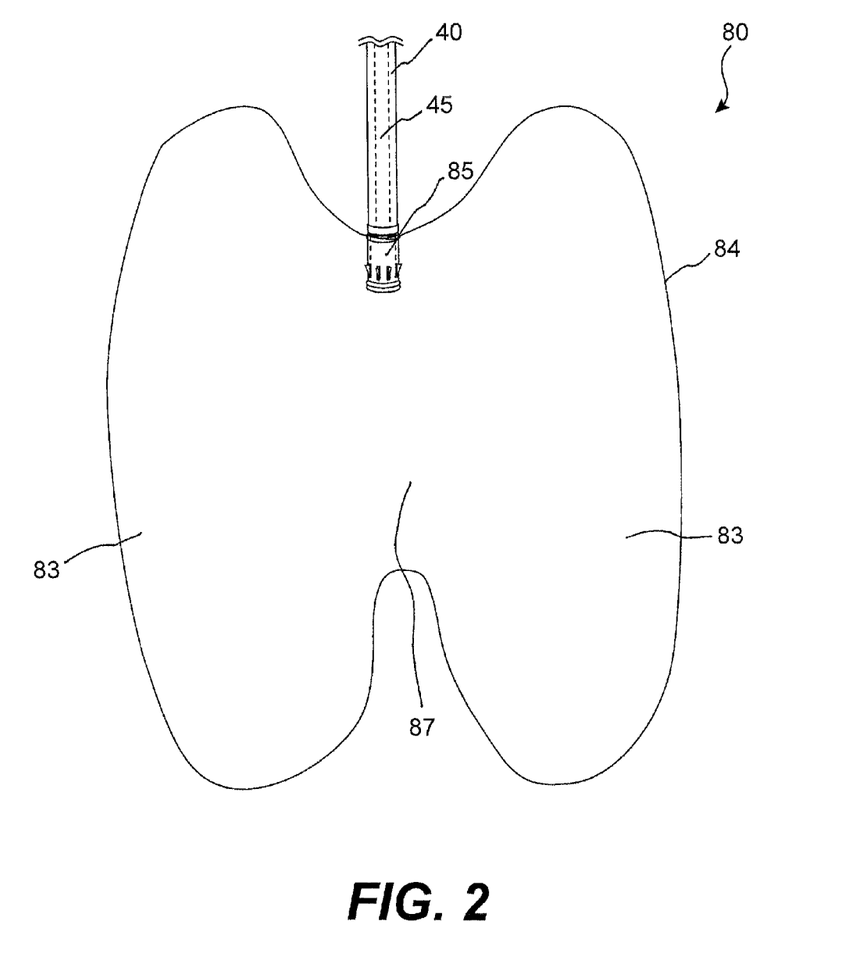
FIG. 2 is a partial view of the balloon catheter of FIG. 1, illustrating the detachable balloon in an inflated state.

Balloon 80 may include a connector body 85 for releasably coupling balloon 80 to shaft 40. A liner 84 that defines a closed inflatable volume of balloon 80 may be fixedly attached to connector body 85. To attach liner 84 to connector body 85, a ring or sleeve 81 integrally formed with liner 84 may be attached to connector body 85. Liner 84 may be made from a permanent implantable material, including, but not limited to, a high-density polyethylene, a linear low-density polyethylene, styrene-isobutylene-styrene block copolymers, silicone, polyurethanes, polyamide block copolymers, or other bioabsorbable materials. Specific examples of such materials may include, but are not limited to, poly(L-lactic acid) (PLLA) or poly(ϵ-caprolactone) (PCL). In an alternative embodiment, liner 84 and connector body 85 may be made of a bioabsorbable or biodegradable material, so that balloon 80 may be allowed to pass through the digestive track after a predetermined period of time and/or after being deflated. Any other suitable material known in the art may be used additionally or alternatively.

When inflated, balloon 80 may have a butterfly shape with two generally rounded side portions 83 and a narrow center portion 87 interconnecting two side portions 83, as shown in FIG. 2. Such a shape may enable balloon 80 to fold in center portion 87 and conform to the wall of the stomach 5 (see, e.g., FIGS. 7 and 8) while ensuring that food can still pass through stomach 5. Further, since a balloon has a natural tendency to flatten out when inflated, two side portions 83 may contact and exert forces against two opposing surfaces of stomach 5, respectively, causing stomach 5 to exert counteracting forces towards balloon 80. The counteracting forces cause balloon 80 to be squeezed in place between the two opposing surfaces of stomach 5.

Connector body 85 may comprise a hollow structure defining an inlet opening of balloon 80 for receiving inflation fluid. Balloon 80 may also include a one-way valve 89 disposed in the inlet opening. One-way valve 89 is configured to only allow inflow of the inflation fluid into balloon 80 while preventing backflow of the inflation fluid from balloon 80. For example, valve 89 may comprise a flap valve or gate seated in the inlet opening and configured to open when the inflation fluid flows into balloon 80 and close when no flow exists in the inlet opening. A flap of the flap valve may be pivotally fixed to connector body 85 via a hinge. To enhance sealing effect between the inlet opening and valve 89, a flexible sealing ring 88 may be fixed to the inlet opening of connector body 85.

Figure 3:
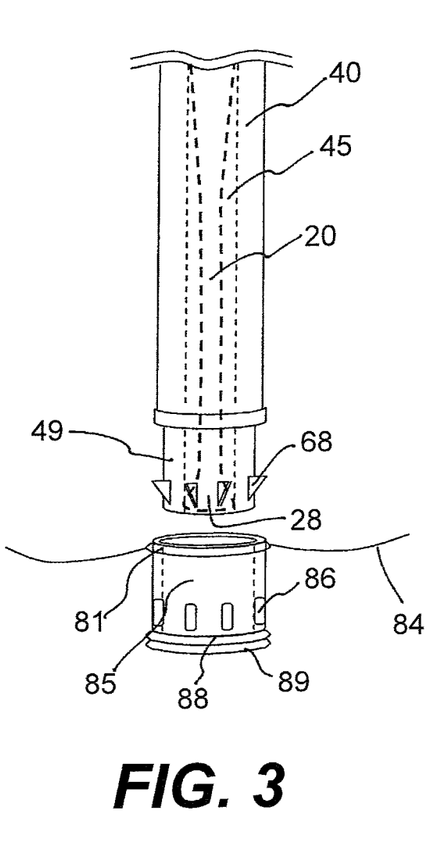
FIG. 3 is a partial, exploded view of the balloon catheter shown in FIGS. 1 and 2, illustrating a configuration of a release mechanism according to one exemplary embodiment.
Figure 4A:
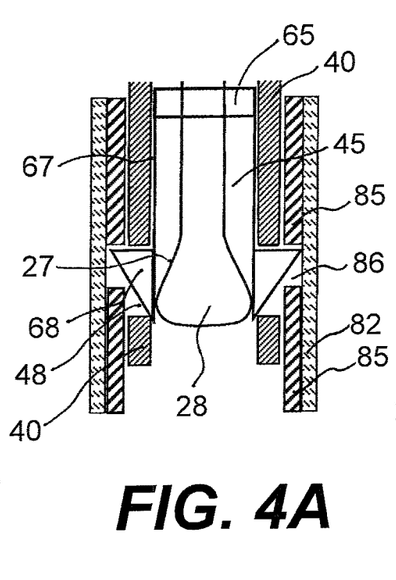
FIGS. 4A and 4B are schematic cross-sectional views of a distal portion of the balloon catheter shown in FIGS. 1-3, illustrating an exemplary operation of the release mechanism.
Figure 4B:
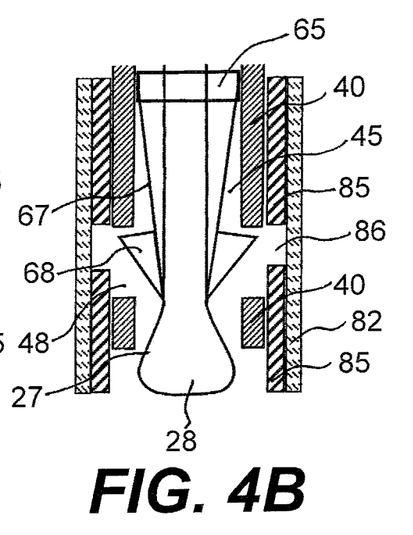

With reference to FIGS. 3, 4A, and 4B, an exemplary embodiment of a releasable coupling between balloon 80 and distal end portion 49 of shaft 40 is described herein. As best shown in FIG. 3, connector body 85 of balloon 80 is configured to receive distal end portion 49 of shaft 40. In some exemplary embodiments, distal end portion 49 may have an outer diameter slightly smaller than that of its main portion such that, when distal end portion 49 is coupled to connector body 85, shaft 40 is flush with the outer surface of connector body 85.

To releasably couple balloon 80 to shaft 40, distal end portion 49 of shaft 40 may include a plurality of movable pins 68 radially disposed around its circumferential surface, and connector body 85 may include a plurality of slots 86 configured to receive corresponding pins 68 of shaft 40. Slots 86 may be sealed with, for example, a sleeve 82 surrounding the outer surface of connector body 85, and the seals (not shown) do not interfere with movable pins 68 inserted into slots 86.

In an alternative embodiment, connector body 85 may form a plurality of grooves (not shown), in place of slots 86, that are configured to receive corresponding pins 68 of shaft 40. The grooves are formed on the inner surface of connector body 85 and may not extend through the entire wall of connector body 85, which may eliminate the need for sealing slots 86.

In an alternative embodiment, distal end portion 49 may include only one movable pin 68, and connector body 85 may include only one slot 86. In another alternative embodiment, connector body 85 may include movable pins 68, and distal end portion 49 may include slots 86 for receiving movable pins 68.

According to some exemplary embodiments, movable pins 68 may be loaded onto or integrally formed with a spring to move in and out of distal end portion 49. For example, as shown in FIGS. 4A and 4B, distal end portion 49 may include a plurality of openings 48 through which pins 68 may protrude from inside lumen 45. Each of pins 68 may be integrally formed with or connected to a corresponding spring leg 67 extending from a band or ring 65 connected to an inner surface of lumen 45. Legs 67 may be made of a memory material biased inwardly towards the center of lumen 45.

To releasably couple balloon 80 to shaft 40, distal end portion 49 of shaft 40 is inserted into connector body 85 with openings 48 and slots 86 aligned with one another. Once openings 48 and slots 86 are aligned, a distal end 28 of plunger 20 is placed underneath spring legs 67 to push legs 67 radially outward, causing pins 68 attached to legs 67 to protrude through openings 48 and slots 86 and to lock connector body 85 of balloon 80 to shaft 40, as shown in FIG. 4A. While pins 68 in the embodiment shown has a triangular shape, pins 68 may have any other suitable shape. Distal end portion 49 and connector body 85 may include appropriate sealing member to seal openings 48 and slots 86 when balloon 80 and shaft 40 are coupled to one another to prevent any leakage of inflation fluid during inflation of balloon 80.

To release balloon 80 from shaft 40, plunger 20 is moved distally relative to shaft 40 to push distal end 28 out of spring legs 67, causing legs 67 to move radially inward. In an alternative embodiment, plunger 20 may be moved proximally relative to shaft 40 to pull distal end 28 out of spring legs 67. When legs 67 are moved inwardly, pins 68 attached to legs 67 are retracted underneath the outer surface of shaft 40, causing connector body 85 of balloon 80 to be freely released from shaft 40, as shown in FIG. 4B. Plunger 28 may have a transition surface 27 along which legs 67 may ride when they move radially inward. Transition surface 27 may also include grooves for receiving distal ends of legs 67.

According to another exemplary embodiment, balloon 80 may be re-coupled to shaft 40. For example, distal end portion 49 of shaft 40 may be re-inserted into connector body 85 to realign openings 48 with slots 86. Connector body 85 may be configured such that its slots 86 automatically align with openings 48 of shaft 40 when shaft 40 is inserted into connector body 85. By way of example, connector body 85 may have a guiding groove formed on the inner surface of connector body 85, and distal end portion 49 of shaft 40 may have a projection configured to be guided by the guiding groove to align its openings 48 with slots 86 of connector body 85. Once openings 48 and slots 86 are aligned, plunger 20 may be pulled proximally relative to shaft 40 to cause legs 67 to ride along transition surface 27 and move radially outward, which in turn causes pins 68 to protrude out of openings 48 and engage slots 86 of connector body 85.

The disclosed configurations for releasable coupling between balloon 80 and shaft 40 are exemplary only. Any suitable coupling and/or release mechanism known in the art may be used additionally or alternatively.

The operation of balloon catheter 10, according to an exemplary embodiment, will be described with reference to FIGS. 1, 2, and 5-8. While operational aspects of the present disclosure will be described in connection with a particular gastric balloon procedure, the present disclosure may be applied to other suitable medical procedures.

FIG. 1 illustrates balloon catheter 10 in a condition for delivery and placement inside a patient's stomach. In this condition, balloon 80 in a deflated state is coupled to distal end portion 49 of shaft 40. To attain the coupling, as described above, plunger 20 is placed in a first position (e.g., shown in FIG. 4A) to push a plurality of movable pins 68 outwardly to engage slots 86 of connector body 85. In some exemplary embodiments, balloon 80 may be compacted to facilitate the delivery into tortuous body cavity. For example, deflated liner 84 of balloon 80 may be wrapped around (e.g., like an umbrella) connector body 85 and/or placed in a compact protective cover (not shown) prior to delivery. Inflation of balloon 80 may automatically unwrap compacted liner 84 or remove the protective cover.

Figure 5:
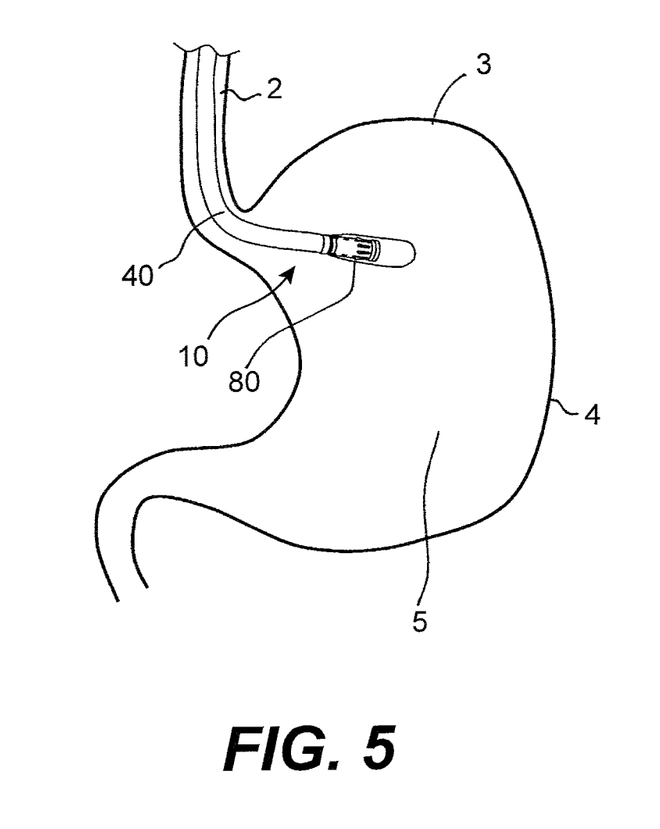
FIGS. 5-7 are schematic illustrations of an exemplary gastric balloon treatment using a balloon catheter of the present disclosure.

With balloon 80 coupled to distal end portion 49 of shaft 40, balloon catheter 10 is directly inserted transorally into the esophagus 2 and into stomach 5, as shown in FIG. 5. A suitable lubrication may be applied to balloon catheter 10 prior to insertion. In some exemplary embodiments, balloon catheter 10 may be inserted into an endoscope lumen to position balloon 80 near a target site inside stomach 5. A suitable imaging device, such as, for example, an endoscope, may be used to aid in positioning of balloon 80 at a desired target site. In an alternative embodiment, instead of inserting balloon catheter 10 transorally, balloon catheter 10 may be inserted laparoscopically into stomach through a small abdominal incision.

Figure 6:
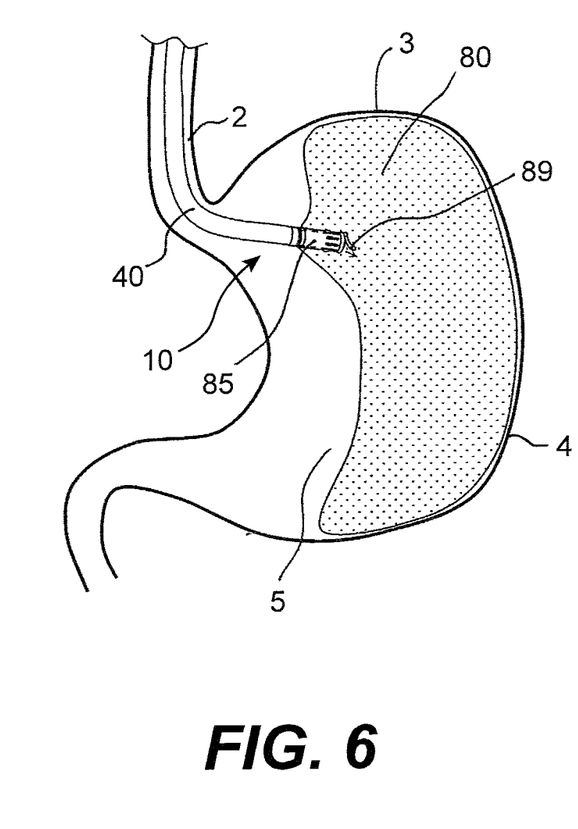

Once balloon 80 releasably coupled to distal end portion 49 of shaft 40 is properly positioned at a desired target site, suitable inflation fluid is supplied to balloon 80 via lumen 25 of plunger 20. As mentioned above, inflation fluid may be supplied to balloon 80 through a separate fluid supply line. The inflation fluid automatically opens one-way valve 89, as shown in FIG. 6.

After balloon 80 is inflated at a desired pressure, inflation fluid can be turned off, which automatically causes valve 89 to close. Placement of one-way valve 89 may eliminate the need for a valving mechanism that requires an actuator to open and close balloon 80 and an elastomeric septum that requires puncturing of a septum by a separate needle assembly to supply inflation fluid.

Figure 7:
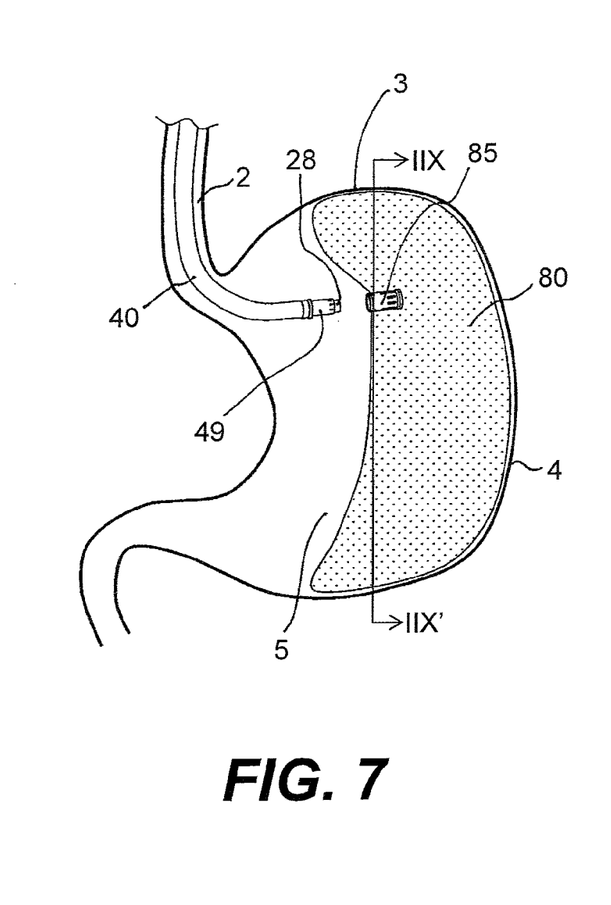

After turning off the inflation fluid and closing valve 89, balloon 80 can be released from distal end portion 49 of shaft 40, as shown in FIG. 7. To release balloon 80 from shaft 40, plunger 20 is moved distally relative to shaft 40 to move its distal end 28 out of spring legs 67, as shown in FIG. 4B, causing movable pins 68 to retract from slots 86. Thereafter, shaft 40 can be pulled proximally to completely disengage shaft 40 from balloon 80. Once balloon 80 is decoupled from shaft 40, shaft 40 can be extracted out of the patient's body, leaving balloon 80 inside stomach 5.

Figure 8:
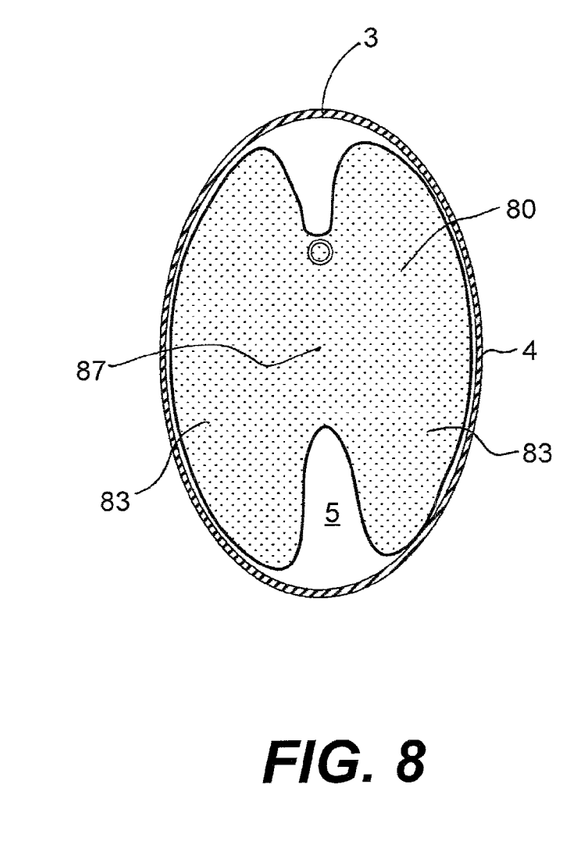
FIG. 8 is a schematic cross-section view along plane IIX-IIX' of FIG. 7.

As shown in FIG. 7, balloon 80 may have a shape that generally conforms to a side wall of stomach 5 extending from the fundus 3 to the greater curvature 4, as shown in FIG. 7. In addition, balloon 80 has narrow center portion 87 interconnecting two side portions 83, as shown in FIGS. 2 and 8, to allow food to pass through the digestive system.

Balloon 80 may remain inside stomach 5 for a predetermined duration of time depending on the choice of balloon material or until the patient's desire to have balloon 80 deflated or removed. Balloon 80 can be allowed to pass through the digestive track after being deflated or degraded. If desired, another balloon may be placed in stomach 5 to achieve desired target weight loss.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A catheter comprising:
   a balloon having an inlet opening for receiving inflation fluid and a one-way valve disposed in the inlet opening to allow inflow of the inflation fluid into the balloon while substantially preventing backflow of the inflation fluid from the balloon, wherein the inflow of the inflation fluid causes the one-way valve to open, and ceasing the inflow of inflation fluid causes the one-way valve to close; and
   an elongated shaft comprising a proximal end, a distal end, and a lumen extending along an axis between the proximal and distal ends, the shaft being configured to supply the inflation fluid to the balloon through the lumen and to releasably couple the balloon to the distal end of the shaft;
   wherein an outer periphery of the balloon, when inflated, comprises a first side portion, a second side portion, and a central portion connecting the first side portion and the second side portion,
   wherein the central portion is narrower than each of the first side portion and the second side portion as measured in a direction of the axis of the shaft; and
   wherein the shaft couples with the balloon at the central portion.

2. The catheter of claim 1, further comprising a plunger movably disposed inside the lumen to actuate a release of the balloon from the distal end of the shaft.

3. The catheter of claim 2, wherein the plunger defines an internal fluid channel having one end configured to connect to a source of the inflation fluid and the other end configured to supply the inflation fluid to the inlet opening of the balloon.

4. The catheter of claim 1, wherein the balloon comprises a connector body configured to releasably engage the distal end of the shaft, the connector body further defining the inlet opening.

5. The catheter of claim 4, wherein the distal end of the shaft comprises a movable pin configured to engage a slot formed in the connector body.

6. The catheter of claim 5, wherein the movable pin is movable from a first position in which the movable pin engages the slot to couple the balloon to the shaft to a second position in which the movable pin disengages the slot to release the balloon from the shaft.

7. The catheter of claim 6, wherein the movable pin is connected to a spring biased to the second position.

8. The catheter of claim 5, further comprising a plunger movably disposed inside the lumen and configured to actuate movement of the movable pin to disengage the movable pin from the slot to release the balloon from the distal end of the shaft.

9. The catheter of claim 4, wherein the one-way valve is attached to the connector body to selectively close the inlet opening.

10. The catheter of claim 4, wherein the connector body comprises a hollow tube configured to receive the distal end of the shaft.

11. The catheter of claim 1, wherein the one-way valve comprises a flap valve mounted to the inlet opening.

12. A method of placing a balloon inside a patient's body, comprising:

inserting into a body passage an elongated shaft having a proximal end, a distal end, and an axis extending between the proximal and distal ends, wherein an inflatable balloon is releasably coupled to the distal end of the shaft;

guiding the shaft to place the balloon at a desired target location inside the patient's body;

supplying inflation fluid to the balloon through an internal lumen of the shaft while the balloon is attached to the distal end of the shaft, wherein an inlet opening of the balloon comprises a one-way valve configured to allow inflow of the inflation fluid into the balloon while substantially preventing backflow of the inflation fluid from the balloon, wherein the inflow of the inflation fluid causes the one-way valve to open, and ceasing the inflow of inflation fluid causes the one-way valve to close, wherein an outer periphery of the balloon, when inflated, comprises a first side portion, a second side portion, and a central portion connecting the first side portion and the second side portion, the central portion being narrower than each of the first side portion and the second side portion as measured in a direction of the axis of the shaft, and wherein the shaft couples with the balloon at the central portion; and releasing the inflated balloon from the distal end of the shaft.

13. The method of claim 12, wherein releasing the balloon from the distal end of the shaft comprises actuating a plunger movably disposed inside the shaft to release the releasable coupling between the balloon and the distal end of the shaft.

14. The method of claim 12, wherein the balloon comprises a connector body configured to releasably couple the distal end of the shaft, and the inlet opening is disposed in the connector body.

15. The method of claim 14, wherein the releasable coupling between the balloon and the distal end of the shaft comprises a movable pin configured to engage a slot formed in the connector body, wherein the movable pin is movable from a first position in which the movable pin engages the slot to couple the balloon to the shaft to a second position in which the movable pin disengages the slot to release the balloon from the shaft.

16. The method of claim 15, wherein releasing the balloon from the distal end of the shaft comprises moving a plunger disposed inside the shaft to cause movement of the movable pin from the first position to the second position.

17. The method of claim 14, wherein the connector body comprises a hollow tube configured to receive the distal end of the shaft.

18. The method of claim 12, wherein the one-way valve comprises a flap valve mounted to the inlet opening.

19. The method of claim 12, wherein the balloon is a gastric balloon, and the step of inserting the shaft into the body passage comprises inserting the shaft transorally into the patient's stomach.

20. The method of claim 19, wherein supplying inflation fluid to the balloon causes the first side portion and the second side portion of the balloon to contact opposing surfaces of the stomach, respectively.

* * * * *